United States Patent [19]

Webler et al.

[11] Patent Number: 4,745,928

[45] Date of Patent: May 24, 1988

[54] RIGHT HEART EJECTION FRACTION AND CARDIAC OUTPUT CATHETER

[75] Inventors: William E. Webler, Laguna Niguel; Edward E. Elson, Anaheim; Michael D. Quinn, El Toro, all of Calif.

[73] Assignee: American Hospital Supply Corporation, Deerfield, Ill.

[21] Appl. No.: 858,448

[22] Filed: May 1, 1986

Related U.S. Application Data

[62] Division of Ser. No. 570,631, Jan. 13, 1984, Pat. No. 4,632,125.

[51] Int. Cl.$^4$ ............................................. A61B 5/02
[52] U.S. Cl. .................................... 128/692; 128/736
[58] Field of Search ............................ 128/691–692, 128/736, 693–694; 73/204; 604/281, 280

[56] References Cited

U.S. PATENT DOCUMENTS

| | | | |
|---|---|---|---|
| 3,405,708 | 10/1968 | Webster, Jr. | 128/692 |
| 3,545,428 | 12/1970 | Webster, Jr. | 128/692 |
| 4,153,048 | 5/1979 | Magrini | 128/692 |
| 4,236,527 | 12/1980 | Newbower et al. | 128/692 |
| 4,329,993 | 5/1982 | Lieber et al. | 128/691 X |
| 4,502,488 | 5/1985 | Degironimo et al. | 128/692 |
| 4,572,206 | 2/1986 | Geddes et al. | 128/692 |
| 4,595,015 | 6/1986 | Jansen et al. | 128/692 X |

*Primary Examiner*—Kyle L. Howell
*Assistant Examiner*—Angela D. Sykes
*Attorney, Agent, or Firm*—Gordon L. Peterson

[57] ABSTRACT

An apparatus for injecting a fluid into the heart and making temperature measurements within the pulmonary artery comprising an elongated flexible tube having a distal end portion, a temperature sensor mounted on the distal end portion, a peripheral wall, at least one lumen extending longitudinally within the tube and an injectate port opening in the peripheral wall proximally of the temperature sensor. The tube can be advanced through a vein, the right atrium and the right ventricle to place the distal end portion in the pulmonary artery and the injectate port in the right atrium facing generally toward the inferior vena cava. The temperature sensor is oriented on the distal end portion so as to materially reduce the likelihood that it will contact the wall of the pulmonary artery during use.

8 Claims, 4 Drawing Sheets

RIGHT HEART EJECTION FRACTION AND CARDIAC OUTPUT CATHETER

This application is a division of application Ser. No. 570,631, filed Jan. 13, 1984, now U.S. Pat. No. 4,632,125.

BACKGROUND OF THE INVENTION

Thermodilution techniques can be used to measure cardiac output. In thermodilution, a bolus of cold saline injectate is injected into the blood steam and allowed to mix with the blood. The resulting temperature change of the mixture can then be used to calculate cardiac output.

It is known to inject the injectate into the vena cava or the right atrium and, in some cases, the right ventricle and to measure the resulting temperature change with a temperature sensor, such as a thermistor, in the pulmonary artery. These functions are commonly carried out with a thermodilution catheter.

For best results for computing cardiac output, it is only necessary that the injectate mix thoroughly and completely with the flowing blood prior to contacting the thermal sensor. Without proper mixing, the cardiac output computed from the thermal curve will not be reliable.

Theoretically, it is possible to use a fast response catheter and thermodilution techniques to calculate right heart ejection fraction. For the best results in calculating right heart ejection fraction, it is necessary that the injectate enter the right ventricle in an abrupt manner as opposed to a slowly decreasing rate. It is also necessary that this injectate be evenly distributed and well mixed throughout the right ventricular volume prior to ejection into the pulmonary artery. When this is done, the temperature sensed in the pulmonary artery represents the mean right ventricular temperature. The prior art has unsuccessfully sought to meet these conditions by injecting directly into the right ventricle and measuring the resulting thermal curve with a thermal sensor which has a relatively rapid response. The lack of success with this approach lies primarily with the mixing requirement described above. Examination of the thermal curves for this prior art approach indicates that the injectate is not evenly distributed and well mixed throughout the ventricle. In addition, these fast response catheters function poorly for determining cardiac output as a result of streaming (uneven distribution and poor mixing) of the injectate. Also, the probability of inducing arrhythmias, especially premature ventricular contractions, is much higher.

The temperature of the mixture in the pulmonary artery changes with each discharge from the right ventricle in a generally step-wise fashion. In order to use thermodilution techniques successfully for the measurement of right heart ejection fraction, it is necessary to measure the beat-to-beat temperature differences of the mixture. Accordingly, it is desirable to use a fast response thermistor, and one such thermistor is shown in a co-pending application of William Webler entitled Apparatus With Fast Response Thermistor and filed on even date herewith. However, the use of a fast response thermistor alone is insufficient due to the tendency of the thermistor to contact the wall of the pulmonary artery. This insulates and shields the thermistor from the flowing mixture and prevents the thermistor from accurately and rapidly measuring the temperature of the mixture.

SUMMARY OF THE INVENTION

This invention provides for the injection of the injectate into the heart so as to obtain a more thorough and even mixing with the blood in the right ventricle while maintaining the abrupt injectate entry condition described above. In addition, this invention reduces the likelihood of contact between the thermistor or other temperature sensor and the wall of the pulmonary artery. Consequently, a catheter embodying these features can be used to measure right heart ejection fraction, as well as cardiac output.

To obtain better mixing, the injectate is injected into the right atrium closely adjacent, e.g., up to 5 centimeters proximal of the tricuspid valve and generally in the direction of the inferior vena cava. Thus, the injectate flows countercurrent to the blood flow from the inferior vena cava, and this provides for thorough mixing and wide distribution of the injectate into the incoming blood. The blood from the superior vena cava holds the mixture in the general region of the tricuspid valve so that the mixture will substantially be completely discharged into the right ventricle. To further enhance mixing and injectate distribution, the injectate port preferably includes at least two adjacent openings.

This mixing proximally of the tricuspid valve can be considered a premixing of the blood and the injectate. When this mixture enters the right ventricle through the tricuspid valve, the mixing characteristics of the right ventricle much more evenly distribute the mixture throughout the right ventricle than occurs with injection directly into the right ventricle. This advantage is the result of premixing and the lack of entry of injectate into the right ventricle during the time of blood ejection into the pulmonary artery.

The likelihood of the temperature sensor contacting the wall of the pulmonary artery so as to insulate and shield the temperature sensor from the ejected blood can be materially reduced by appropriately orienting the temperature sensor circumferentially of the catheter tube on which it is mounted. In the past, thermistors were randomly oriented on thermodilution catheters. Although the temperature sensor could be kept out of contact with the pulmonary artery wall with projections on the catheter tube, controlling of the orientation is much better because it requires no additional parts and it produces no obstructions.

In a preferred embodiment, the temperature sensor is mounted on a distal end portion of a flexible catheter tube. For thermodilution, the catheter tube, which is sized to pass through a vein or an artery, extends through the right atrium and the right ventricle to the pulmonary artery. This positions the distal end portion of the catheter tube in the pulmonary artery. The distal end portion is preferably preformed into a curve, but in any event, when the catheter tube is in the position described above, the distal end portion is curved at least somewhat.

It has been found that the temperature sensor does not tend to contact the wall of the pulmonary artery if it is located in a zone which extends circumferentially of the tube for about 150 degrees and which extends to the outside of the curve of the distal end portion no more than about 30 degrees. In use, the catheter tube is oriented so that such zone primarily faces anteriorly, i.e., so that such zone is on the upper side of the curve when the patient is reclining on his back.

It has been found that liquid flow through the pulmonary artery at the curved distal end portion tends to push the distal end portion toward the outside of the curve so as to move the outside of the curve toward, and sometimes into engagement with, the pulmonary artery wall. Thus, by orienting the temperature sensor toward the inside of the curve, normal flow through the pulmonary artery tends to hold the temperature sensor away from this part of the pulmonary artery wall.

Thermodilution is typically carried out with the patient on his back. It has been found that the flow of fluid through the pulmonary artery rarely, if ever, tends to elevate the upper or top side of the distal end portion of the catheter tube into contact with the pulmonary artery wall whereas the lower side or bottom of the distal end portion may contact the pulmonary artery wall. For this reason, it is preferred to locate the temperature sensor in the top 180 degrees of the catheter tube. By summing these two location parameters, it can be seen that the temperature sensor should be located in the upper inside quadrant of the catheter tube, and it has been found that the 150-degree zone defined above defines a reasonable workable range.

The preferred location for the temperature sensor is at the junction between the inside of the curve and the outside of the curve. In other words, when the catheter is in use on a patient reclining on his back, the preferred location for the temperature sensor is at the top of the curve. The reason for this is that this location provides the temperature sensor with the most rapid response. This is believed to be the result of placing the catheter where the velocity of the blood-injectate mixture over it is at a maximum, i.e., where the flow of the mixture is not materially interrupted by the catheter tube.

As the location of the temperature sensor is rotated from the optimum location described above, the response time slows. However, the response time slows much more rapidly as the temperature sensor is moved into the outside of the curve. Accordingly, the preferred location of the temperature sensor for production purposes is on the inside of the curve closely adjacent the optimum position. For example, the temperature sensor may have a central axis which is displaced 20 degrees toward the inside of the curve from the optimum location.

The temperature sensor must be small and may be a thermistor. In order to improve the response of the temperature sensor, at least a portion of the temperature sensor is displaced radially from the longitudinal axis of the catheter tube so as to get the temperature sensor relatively close to the fluid, the temperature of which is to be sensed. It is this radially displaced portion of the temperature sensor which should be positioned in the circumferentially extending zone as described above. Of course, portions of the thermistor, particularly those portions which are not contributing significantly to its rapid response, may be located out of the above-described circumferentially extending zone.

Although the functions of injecting the cold injectate toward the inferior vena cava and temperature sensing in the pulmonary artery can be carried out with separate catheter tubes, preferably a single catheter tube provides both of these functions. When these functions are carried out with the same catheter tube, the orientation of the injectate port can be defined with relation to the distal curve. In addition, the orientation of the injectate port can also be defined with reference to the circumferential orientation of the temperature sensor. If the injectate port comprises multiple, circumferentially spaced openings, the central or geometric axis of these openings can be oriented circumferentially relative to either or both of the distal curve and the circumferential orientation of the temperature sensor.

Structurally, the catheter tube may include a peripheral wall, at least one lumen extending longitudinally of the tube, and the injectate port, which opens in the peripheral wall proximally of the temperature sensor. Proximal and distal electrodes may also be mounted on the catheter tube, if desired. The catheter tube may also include an infusion lumen and an infusion port. Of course, the catheter may have other lumens for providing various other useful functions.

The invention, together with additional features and advantages thereof, may best be understood by reference to the following description taken in connection with the accompanying illustrative drawing.

BRIEF DESCRIPTION OF THE PREFERRED EMBODIMENT

Figures 1, 2:
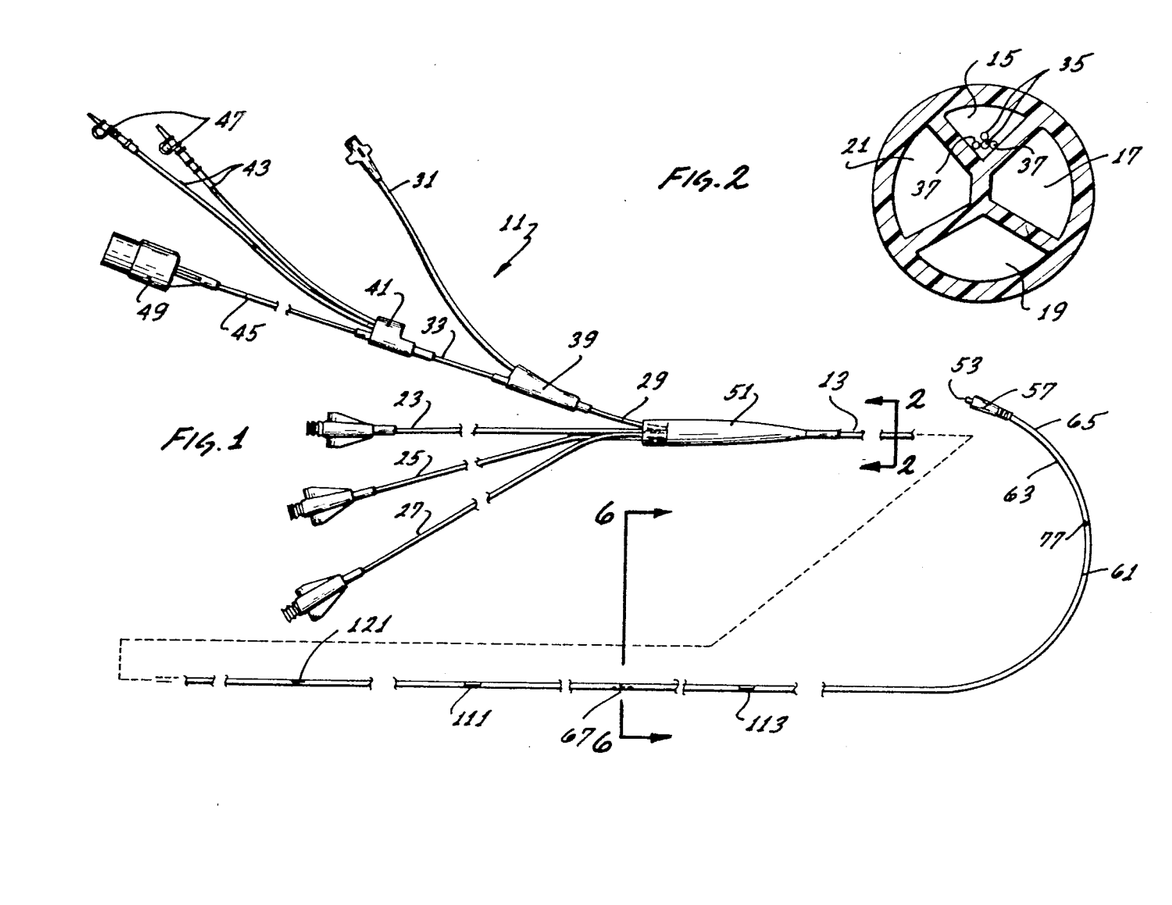
FIG. 1 is a plan view of a catheter constructed in accordance with the teachings of this invention with the injectate port rotated slightly from its true position.
FIG. 2 is an enlarged sectional view taken generally along line 2—2 of FIG. 1.
Figures 3, 4:
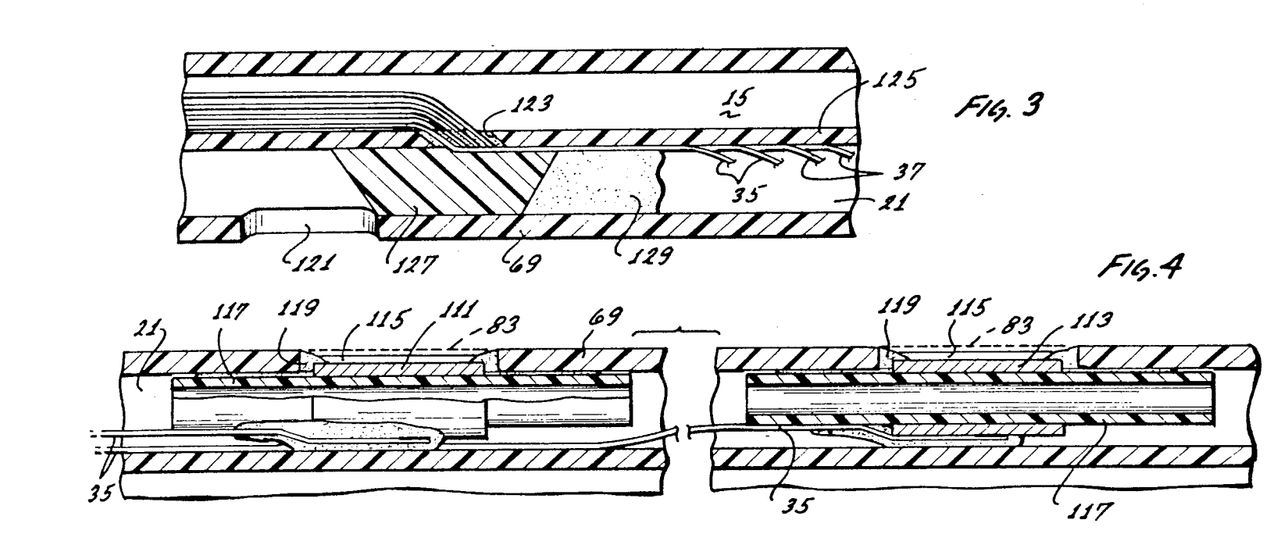
FIGS. 3-5 are enlarged longitudinal, fragmentary, sectional views showing the catheter tube adjacent the infusion port, the two electrodes and the injectate port, respectively.
Figure 7:
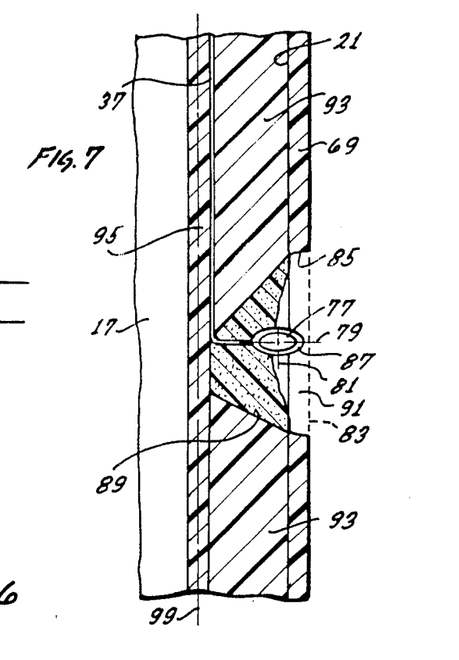
FIGS. 7 and 8 are enlarged, fragmentary, sectional views taken generally along lines 7—7 and 8—8, respectively, of FIG. 6 and illustrating a preferred construction of, and mounting structure for, the temperature sensor.

FIG. 1 shows an apparatus in the form of a catheter 11 which comprises an elongated catheter tube 13 having a balloon inflation lumen 15 (FIG. 2), a through lumen 17, an injectate lumen 19, and an infusion lumen 21. A pressure monitoring tube 23, an injectate tube 25 and an infusion tube 27 are fused to the tube 13 within the through lumen 17, the injectate lumen 19 and the infusion lumen 21, respectively. A tube 29 is fused to the tube 13 within the balloon inflation lumen 15 and is joined to an inflation tube 31 and a conduit 33 for insulated electrode leads 35 (FIGS. 2 and 4) and thermistor leads 37 (FIGS. 2 and 7) by a coupler 39. The electrode leads 35 and the thermistor leads 37 are separated in a connector 41 which couples the electrode leads 35 into separate conduits 43 and couples the thermistor leads into a conduit 45. The leads 35 and 37 can be coupled to an appropriate electronic monitoring device (not shown) by couplers 47 and 49, respectively.

The catheter tube 13 may be extruded from a suitable biocompatible plastic material. The catheter tube 13 is flexible, elongated and sized to be received within a vein or an artery. The catheter tube has a proximal end within a flexible sleeve 51, which encases the distal ends of the tubes 23, 25, 27 and 29 and a distal end 53.

The balloon inflation lumen 15 extends continuously from the proximal end of the tube 13 to a location just distally of a port 55 (FIG. 9) which provides communication between the balloon inflation lumen and a balloon 57 which is located closely adjacent the distal end 53. The balloon 57 and the manner in which it is inflated through the balloon inflation lumen 15 are conventional.

Figure 9:
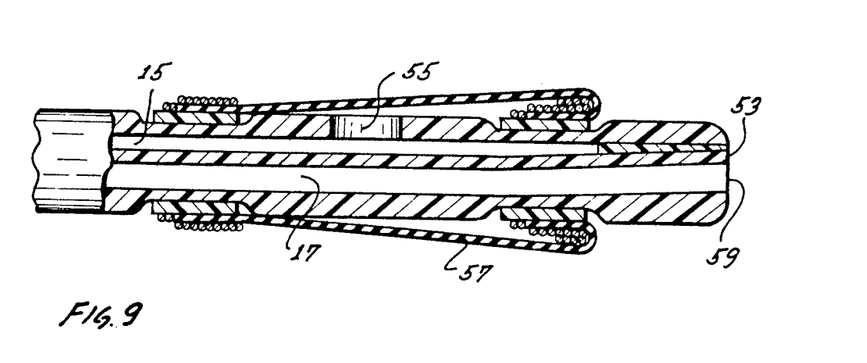
FIG. 9 is an enlarged, fragmentary, sectional view showing the distal tip of the catheter.

The through lumen 17 extends continuously from the proximal end of the catheter tube 13 to the distal end 53 where it opens at a distal port 59 (FIG. 9). The through lumen 17 can be used, for example, to monitor pressures within the body.

As shown in FIG. 1, the catheter tube 13 has a curved distal end portion 61. The curve in the distal end portion 61 is preformed in that the distal end portion assumes this curved configuration when it is under no external force. Although the curve may be of varying lengths and radii, in the embodiment illustrated, the curve extends for approximately 170 degrees, begins at a location about four inches from the distal end 53 and terminates at the distal end. The curve has an inside 63, i.e., a concave surface as viewed in FIG. 1, and an outside 65, i.e., a convex surface as viewed in FIG. 1, and in the embodiment illustrated, lies in a single plane. Generally, the configuration of the curved distal end portion 61 is such as to permit proper orientation and positioning of the distal end portion 61 in the pulmonary artery as described more fully hereinbelow.

Figure 5:
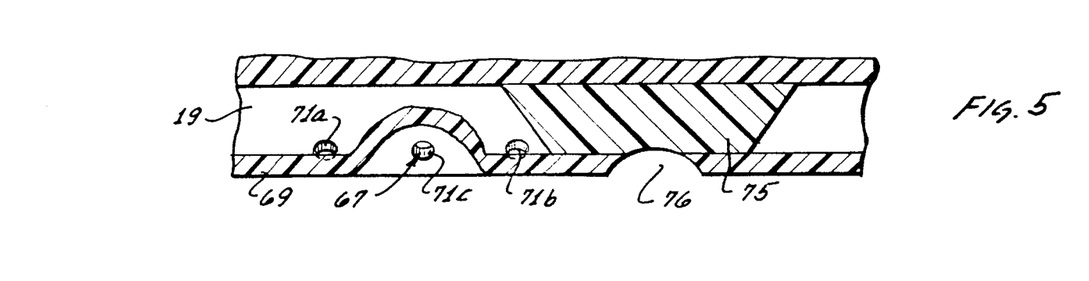

The injectate lumen 19 extends continuously from the proximal end of the catheter tube 13 to a location proximally of the curved distal end portion 61. An injectate port 67 (FIGS. 1 and 5) extends through a peripheral wall 69 of the catheter tube 13 to provide communication between the injectate lumen 19 and the exterior of the tube. Preferably, the injectate port 67 comprises a plurality of openings, and in the embodiment illustrated, three of such openings are provided. Although various patterns are possible, in the embodiment illustrated, the injectate port 67 includes proximal and distal openings 71a and 71b in axial alignment, and an intermediate opening 71c slightly circumferentially spaced from an axial line joining the two aligned openings 71a and 71b and half-way between the two aligned openings. Thus, the three openings are arranged to form a triangle, and the injectate port 67 has a central axis 73 (FIGS. 6) in the form of a radial line extending through the centroid of the triangle. For example, the centerlines of the openings 71a and 71b may be spaced 0.075 inch axially of the intermediate opening 71c and 0.025 inch circumferentially of the intermediate opening 71c, and the centerline of the proximal opening 71a may be about 8.27 inch from the distal end 53.

The injectate port 67 is located so that it will be in the right atrium closely adjacent the tricuspid valve and in proximity to the inferior vena cava when the catheter is in position in the heart as described more fully hereinbelow with reference to FIG. 10. The lumen 19 is closed by a plug 75 (FIG. 5) just distally of the injectate port 67, and the plug can be inserted through an opening 76 in the peripheral wall 69.

A temperature sensor in the form of a thermistor 77 is mounted on the distal end portion 61 of the catheter tube 13. The thermistor 77 should be a fast response thermistor when mounted and preferably has a response time which is rapid enough to measure the temperature changes within the interval between heart beats. For example, an average mounted response time of 100 to 150 milliseconds or less should be adequate. Although various temperature sensors and temperature sensor mounting constructions can be employed, it is preferred to use a thermistor in the form of a thermistor bead mounted as described in the above referred to co-pending application entitled Apparatus With Fast Response Thermistor which is incorporated by reference herein.

Briefly however, the thermistor 77 has a major or central axis 79 and a minor axis 81, and it is mounted upright in the infusion lumen 21 with the radial outer end of the thermistor lying below a catheter body line 83, i.e., an extension of the cylindrical periphery of the catheter tube 13 over an opening 85 in the peripheral wall 69 at the thermistor 77. The major axis 79 extends radially.

The thermistor 77 is completely covered with, and encapsulated in, a thin layer 87 of insulating adhesive material, such as one or more thin coatings of vinyl and/or urethane to provide saline protection. The thermistor 77 is mounted by a mounting body 89 which is in the lumen 21 adjacent the opening 85. The mounting body 89 cooperates with the tube 13 to define a cavity 91 at the opening which opens radially outwardly. The mounting body 89 may be constructed of urethane or other suitable biocompatible electrical and thermal-insulating adhesive material. The mounting body 89 is located between plugs 93 which block the lumen 21 on opposite sides of the opening 85. About one half of the thermistor 77 projects radially beyond the mounting body. The thermistor leads 37 extend from the thermistor 77 between the proximal plug 93 and a partition 95 between the lumens 21 and 17 proximally to the tube 29 as described more fully hereinbelow with reference to FIG. 3. For example, the thermistor may be about 1.55 inches from the distal end 53.

Figure 8:
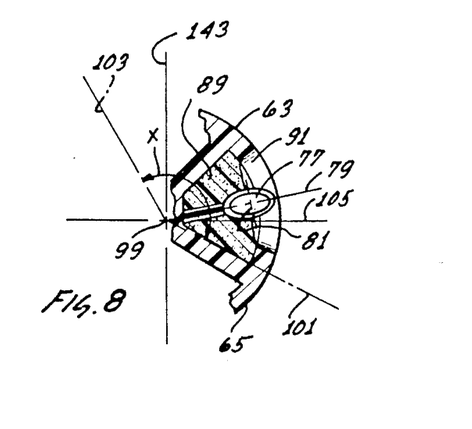

One feature of this invention is the orientation of the thermistor 77 on the curved distal end portion 61. More specifically, the thermistor 77 is displaced radially from a longitudinal axis 99 (FIGS. 6-8) of the catheter tube 13 and is at a location in a zone which extends circumferentially of the tube for about 150 degrees and which extends into the outside 65 of the curve of the distal end portion 61 for 30 degrees. The boundaries of this circumferentially extending zone are radial reference lines 101 and 103 (FIG. 8) which intersect at the axis 99 to define an interior angle "X" of 150 degrees. The reference line 101 extends into the outside 65 of the curve for 30 degrees as shown in FIG. 8. If the thermistor 77 is rotated clockwise (as viewed in FIG. 8) beyond the reference line 101, it is so far into the outside 65 of the curve that there is danger that it may contact the wall of the pulmonary artery when in use due to the tendency of the catheter tube to be moved in a direction toward the outside 65 of the curve. If the thermistor 77 is rotated counterclockwise (as viewed in FIG. 8) beyond the reference line 103, there is increased risk that it will contact the wall of the pulmonary artery when in use due to the tendency of the catheter tube to lie at a relatively low level in the pulmonary artery when the patient is reclining on his back.

The location of the thermistor 77 which produces the fastest response is the location in which the major axis 79 is aligned with, or closely adjacent, the reference line 105, i.e., at the juncture of the inside 63 and the outside 65 of the curve. However, to provide the desired production tolerances and assure that the thermistor, when used does not extend materially into the outside 65 of the curve, the thermistor 77, when the catheter is constructed and packaged, preferably lies entirely on the inside 63 of the curve. For example, the major axis 79 may form a 20-degree angle with the reference line 105.

Figure 6:
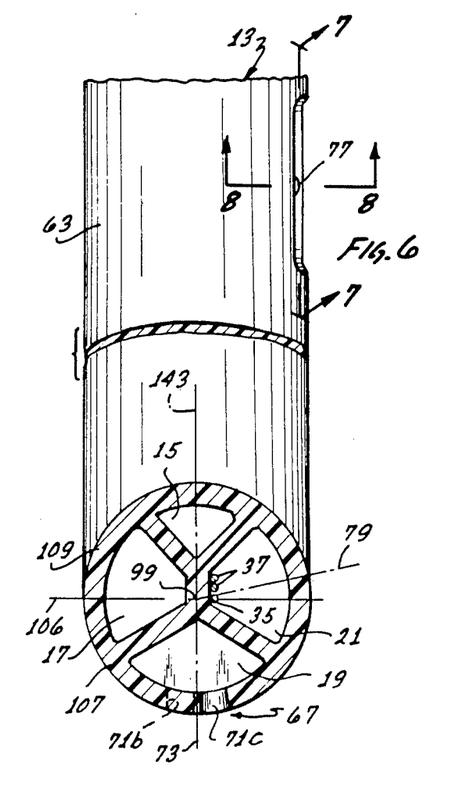
FIG. 6 is an enlarged, fragmentary, sectional view taken generally along line 6—6 of FIG. 1.

Another feature of the invention is the orientation of the injectate port 67 relative to the curved distal end portion 61. In this regard, the catheter tube 13 may be considered as having a dividing plane 106 (FIG. 6) which separates the outside 65 of the curve from the inside 63 of the curve and which extends along the longitudinal axis 99 of the tube 13 to divide the tube longitudinally into first and second half sections 107 and 109 which include the outside 65 and the inside 63 of the curve, respectively. The reference line 105 lies in the dividing plane 106. The central axis 73 of the injectate port 67 is in the first half section 107 of the tube 13. With this orientation, the injectate port is located and oriented on the tube 13 so that injectate can be injected through the injectate lumen 25 and the injectate port 67 generally toward the inferior vena cava as described hereinbelow with reference to FIG. 10. In a preferred construction, the central axis 73 of the injectate port 67 is perpendicular to the dividing plane 105. The openings 71b and 71c are on opposite sides of the axis 73 as shown in FIG. 6.

The orientation of the injectate port 67 can also be defined with reference to the orientation of the central radial axis 79 of the thermistor 77. As shown in FIG. 6, the axis 79 is displaced approximately 110 degrees from the central axis 73. In FIG. 6, the central axis 79 of the thermistor 77 is transferred to the cutting plane of FIG. 6. For optimum results, in use the axes 73 and 79 in FIG. 6 should form about a 90-degree angle, but when considering tolerances as discussed above, the preferred angle is greater than 90 degrees and may be about 120 degrees.

As an option, the catheter 11 may include a proximal electrode 111 located proximally of the injectate port 67 and a distal electrode 113 (FIGS. 1 and 4) located between the injectate port and the distal end portion 61. Although the electrodes 111 and 113 can be of any suitable construction, they are preferably constructed as described in a copending application of William Webler and Clement Lieber entitled Lumen Mounted Electrodes For Pacing and Intra-cardiac ECG Sensing which was filed on even date herewith and which is incorporated herein by reference.

Briefly, the electrodes 111 and 113 and their mounting structures are identical, and each of the electrodes is in the form of a tubular conductive member or sleeve of suitable conductive, biocompatible metal. The catheter tube 13 has openings 115 in the peripheral wall 69 for exposing portions of the electrodes 111 and 113, respectively.

The mounting means for the electrode 111 includes a tubular, resilient, bendable mounting member 117 of a suitable nontoxic plastic material and an insulating adhesive 119 which bonds the electrode 111 to the mounting member 117 and bonds both of these members to the catheter tube 13 within the infusion lumen 21. The mounting member 117 extends completely through the electrode 111 and has end portions in the infusion lumen 21 on the opposite sides of the electrodes to mechanically interlock with the catheter tube.

The insulation is stripped from the distal ends of the electrode leads 35, and the distal ends are spot welded to the electrodes 111 and 113, respectively, and are further bonded to the associated electrode and mounting member by a portion of the insulating adhesive 119. The electrodes 111 and 113 lie below the catheter body line 83. The openings 115 extend circumferentially to expose the desired circumferential portion of the electrodes, such as about one-fourth of the periphery of the electrodes. The electrode leads 35 extend proximally into the tube 29.

The catheter tube 13 preferably has an infusion port 121 in the peripheral wall 69 proximally of the proximal electrode 111 which provides communication between the infusion lumen 21 and the exterior of the catheter. This enables the catheter 11 to be used to infuse various fluids through the infusion lumen 21 and the infusion port 121 into the heart.

Although the electrode leads 35 and the thermistor leads 37 can be conducted proximally through the catheter tube 13 in various different ways, in the embodiment illustrated, these leads extend proximally through the infusion lumen 21, an opening 123 (FIG. 3) in a partition 125 and the balloon inflation lumen 15 to the tube 29. The opening 123 is sealed with an adhesive. In addition, the opening 123 and the infusion port 121 are sealed by a plug 127 in the infusion lumen 21 just distally of the infusion port 121 and by a mass of insulating adhesive 129 adjacent the plug.

In use, the catheter tube 13 is inserted through a vein of a patient and into the heart (FIG. 10) using known techniques. The insertion is preferably an upper body insertion and, for proper orientation in the heart, the insertion should be carried out with the thermistor 77 facing the patient's anterior aspect. The balloon 57 is inflated through the balloon inflation lumen 15 and the port 55, and the inflated balloon is used to carry the distal end portion 61 of the catheter 11 to the pulmonary artery 131. Because the thermistor 77 and the electrodes 111 and 113 are mounted below the body line 83, they will not rub against any introducer which is used, either during the insertion or the withdrawal of the catheter tube 13.

In order to obtain data from which right heart ejection fraction and cardiac output can be obtained, the catheter tube 13 is inserted so as to place the thermistor 77 in the pulmonary artery, and the injectate port 67 in the right atrium 133 facing generally toward the inferior vena cava 135. The injectate port 67 is located proximally of, and closely adjacent, the tricuspid valve 137. Preferably, the injectate port is within about five centimeters of the tricuspid valve, although the actual distance will vary from patient to patient depending on anatomical insertion technique considerations.

The curve of the distal end portion 61 may be deflected somewhat in the pulmonary artery. In any event, the curved distal end portion 61 is used to orient the catheter tube in a known manner in the heart. When so oriented, the thermistor 77 lies within the circumferentially extending zone described above, and the injectate port 67 is also oriented as described above. If the catheter tube 13 is oriented within the heart using other techniques, the distal end portion 61 need not be curved.

With this orientation of the catheter tube 13, the distal electrode 113 is in the right ventricle 139, and the proximal electrode 111 is in the superior vena cava 141. The infusion port 121 is also in the superior vena cava 141.

By inserting the catheter tube 13 with the thermistor 77 facing the patient's anterior aspect, the thermistor faces anteriorly or upwardly when the patient is reclining on his back. With reference to FIGS. 6 and 8, the anterior portion of the catheter tube 13 is the half of the tube to the right of a reference plane 143. All but 30 degrees of the circumferentially extending zone defined by the angle "X" faces anteriorly, and thus, the zone faces primarily anteriorly. In the illustrated embodiment, the thermistor faces anteriorly and lies slightly toward the inside 63 of the curve.

To determine right heart ejection fraction or cardiac output, a bolus of cold injectate, such as saline solution, is rapidly injected over several heart beats through the injectate lumen 19 and the injectate port 67 generally toward the inferior vena cava 135. The injection of the injectate through the multiple openings 71a–71c countercurrent to the blood flow from the inferior vena cava causes a wide distribution of the injectate into the blood and provides for good mixing. The blood flow from the superior vena cava 141 tends to hold the mixture in the region of the tricuspid valve 137 so that, upon opening of the tricuspid valve, substantially all of the mixture is discharged into the right ventricle 139 and can ultimately pass over the thermistor 77 in the pulmonary artery 131.

Figure 10:
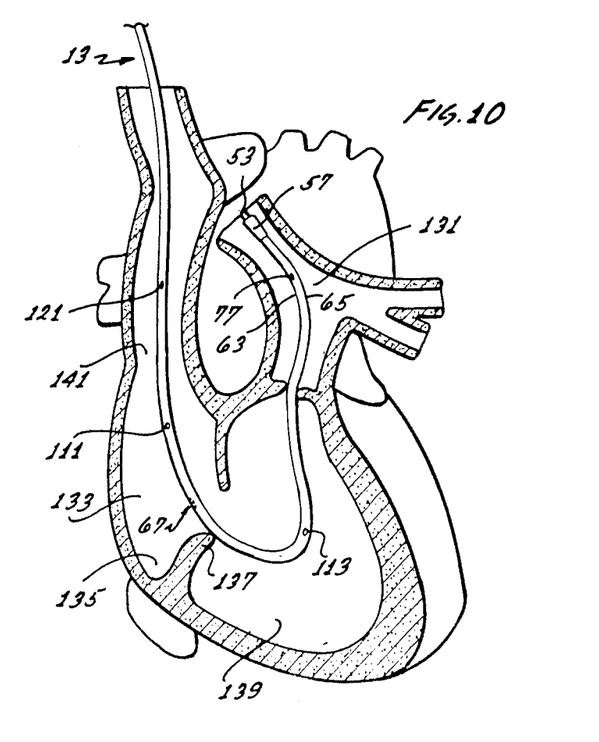
FIG. 10 is a sectional view of a human heart with the catheter in position.

The flow of blood and the mixture past the distal end portion 61 tends to move the distal end portion toward the outside 65 of the curve, i.e., generally toward the right as viewed in FIG. 10 and into engagement with the wall of the pulmonary artery. Also, the distal end portion tends to move posteriorly, i.e., downwardly with the patient reclined on his back. However, because the thermistor 77 is oriented anteriorly and somewhat toward the inside 63 of the curve, it does not contact the pulmonary artery wall. Consequently, the pulmonary artery wall does not insulate the thermistor 77 from the mixture and it can rapidly and accurately track the temperature change of the mixture in the pulmonary artery which is assumed to be the same temperature that exists within the right ventricle. The temperature information obtained by the thermistor 77 is transmitted proximally along the thermistor leads 37 to appropriate electronic apparatus (not shown) which calculates right heart ejection fraction and cardiac output.

For example, right heart ejection fraction can be calculated using the following equation:

$$EF = 1 - \frac{T_B - T_2}{T_B - T_1}$$

where,

EF is right heart ejection fraction;

$T_B$ is the base temperature of the blood as measured by the thermistor 77, i.e., the temperature of the blood, without injectate added to it;

$T_1$ is the temperature of the mixture as measured by the thermistor 77 one heart beat following the measurement of the lowest temperature of the blood-injectate mixture recorded by the thermistor; and $T_2$ is the temperature of the blood-injectate mixture as measured by the thermistor 77 one heart beat after the measurement of the temperature $T_1$.

Figure 11:
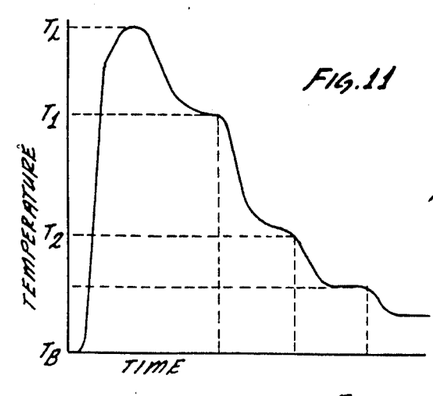
FIG. 11 is a plot of temperature versus time for the blood-injectate mixture in the pulmonary artery with higher temperatures shown lower on the ordinate than lower temperatures.

FIG. 11 is a thermal curve showing an example of the variation in temperature of the blood-injectate mixture with time, with the injectate being injected over a single heart beat. In FIG. 11, the temperatures increase toward the origin so that $T_L$ is a lower temperature than $T_1$.

With reference to FIG. 11, it can be seen that the mixture reaches its lowest temperature $T_L$, and thereafter the temperature increases in steps or increments as illustrated. The temperature $T_1$ is measured at the first step following measurement of $T_L$ and this occurs one heart beat after the measurement of $T_L$. The temperature $T_2$ is measured at the second step following $T_L$ and this occurs two heart beats after the measurement of $T_L$.

An optional, but preferred, feature of the invention is to coat the catheter tube 13 on its exterior surface and on the interior surfaces defining the lumens 15, 17, 19 and 21 with heparin for the purpose of reducing the tendency of the catheter to induce clotting of the blood. Although the heparin coating of catheters for this purpose is known per se, the heparin coating is of particular advantage for the catheter 11 in that the cavity 91 adjacent the thermistor 77 provides an irregularity in the catheter's outer surface which is more likely to induce clotting than if this irregularity were not present.

Although an exemplary embodiment of the invention has been shown and described, many changes, modifications and substitutions may be made by one having ordinary skill in the art without necessarily departing from the spirit and scope of this invention.

We claim:

1. An apparatus for injecting an injectate into the heart and making temperature measurements, said apparatus comprising:

an elongated flexible tube having a longitudinal axis, proximal and distal ends, a distal end portion which includes said distal end, a peripheral wall, at least one lumen extending longitudinally within the tube and an injectate port opening in said peripheral wall;

said tube being sized to pass through a vein, the right atrium and the right ventricle to the pulmonary artery with the distal end portion being positionable in the pulmonary artery;

a temperature sensor;

means for mounting the temperature sensor on said distal end portion of the tube whereby the temperature sensor is adapted to be positioned in the pulmonary artery and can obtain temperature information about fluid in the pulmonary artery, said injectate port opening proximally of the temperature sensor and being about 21 centimeters from the distal end;

means for transmitting the temperature information proximally of the temperature sensor along the tube;

said injectate port being located and oriented on said tube so that the injectate port is in the right atrium closely adjacent the tricuspid valve and so that injectate can be injected through the lumen and the injectate port generally toward the inferior vena cava and countercurrent to the blood flow from the inferior vena cava, and said distal end portion being curved with such curve having an inside and an outside, said injectate port being located proximally of the curved distal end portion, said tube having a dividing plane which separates the outside of the curve from the inside of the curve and which extends along the longitudinal axis of the tube to divide the tube longitudinally into first and second half sections which include the outside and the inside of the curve, respectively, and said injectate port has a central axis in the first half section of the tube.

2. An apparatus as defined in claim 1 wherein said injectate port comprises a plurality of openings.

3. A method for injecting an injectate into the heart and making temperature measurements within the pulmonary artery of a patient comprising:
providing an elongated flexible tube sized to pass through a vein or an artery and into the heart with said tube having a longitudinal axis, proximal and distal end, a distal end portion which includes said distal end, a peripheral wall, at least one lumen extending longitudinally within the tube and an injectate port opening in said peripheral wall;
inserting the flexible tube through a vein into heart to place the injectate port proximally of and within about five centimeters of the tricuspid valve and facing generally toward the inferior vena cava so that the injectate port can inject the injectate countercurrent to the blood flow from the inferior vena cava;
injecting an injectate through the lumen and the injectate port generally toward the inferior vena cava so that the injectate flows countercurrent to the blood flow from the inferior vena cava and allowing the injectate to mix with the blood to form a mixture; and
measure the temperature of the mixture in the pulmonary artery.

4. A method as defined in claim 3 wherein said step of providing includes providing a temperature sensor on the distal end portion of the tube and carrying out said step of measuring utilizing the temperature sensor.

5. A method as defined in claim 3 wherein the injectate port comprises a plurality of openings and the step of injecting includes injecting the cold injectate through said openings.

6. A method as defined in claim 3 wherein said step of measuring includes determining the temperatures of the mixture in the right ventricle at least at two different times and utilizing the temperatures so determined to ascertain right heart ejection fraction.

7. A method for injecting injectate into the heart and making temperature measurements within the pulmonary artery of a patient comprising:
providing an elongated flexible tube sized to pass through a vein or an artery and into the heart with said tube having a longitudinal axis, proximal and distal ends, a distal end portion which includes said distal end, a peripheral wall, at least one lumen extending longitudinally within the tube and an injectate port opening in said peripheral wall;
inerting the flexible tube through a vein into the heart to place the injectate port proximally of and closely adjacent the tricuspid valve and facing generally toward the inferior vena cava so that the injectate port can inject the injectate countercurrent to the blood flow from the interior vena cava;
injecting an injectate through the lumen and the injectate port generally toward the inferior vena cava so that the injectate flows countercurrent to the blood flow from the inferior vena cava to mix the injectate with the blood to form a mixture; and
measuring the temperature of the mixture in the pulmonary artery.

8. A method as defined in claim 7 wherein said step of providing includes providing an infusion lumen in the tube and an infusion port in the tube communicating with the infusion lumen with the infusion port being located proximally of the injectate port, said step of providing including providing a proximal electrode intermediate said port and said step of inserting places the infusion port and the proximal electrode in the superior vena cava.

* * * * *